US006369892B2

(12) United States Patent
Richert

(10) Patent No.: US 6,369,892 B2
(45) Date of Patent: Apr. 9, 2002

(54) METHOD FOR DISCRIMINATION OF PRODUCE

(76) Inventor: Gerald R. Richert, 45834 C Sierra Dr., Three Rivers, CA (US) 93271

( * ) Notice: Subject to any disclaimer, the term of this patent is extended or adjusted under 35 U.S.C. 154(b) by 0 days.

(21) Appl. No.: 09/766,680

(22) Filed: Jan. 18, 2001

Related U.S. Application Data

(62) Division of application No. 09/100,286, filed on Jun. 19, 1998.

(51) Int. Cl.7 .................................................. G01J 3/46
(52) U.S. Cl. ........................ 356/402; 356/628; 356/446
(58) Field of Search ............................... 356/628, 402, 356/408, 448, 446

(56) References Cited

U.S. PATENT DOCUMENTS

| | | | |
|---|---|---|---|
| 3,630,619 A | 12/1971 | Rosen | 356/74 |
| 3,942,154 A | 3/1976 | Akami et al. | 340/146.3 B |
| 3,945,729 A | 3/1976 | Rosen | 356/5 |
| 4,106,628 A | 8/1978 | Warkentin | 209/74 |
| 4,247,202 A | 1/1981 | Failes | 356/310 |
| 4,330,062 A | 5/1982 | Conway et al. | 209/582 |
| 4,825,068 A | 4/1989 | Suzuki et al. | 250/223 R |
| 4,959,244 A | 9/1990 | Penney et al. | 427/53.1 |
| 4,961,489 A | 10/1990 | Warkentin | 198/365 |
| 5,018,864 A | 5/1991 | Richert | 356/372 |
| 5,029,692 A | 7/1991 | Warkentin | 198/365 |
| 5,090,807 A | 2/1992 | Tai | 356/310 |
| 5,106,195 A * | 4/1992 | Richert | 356/407 |
| 5,156,278 A * | 10/1992 | Aaron et al. | 209/556 |
| 5,195,628 A | 3/1993 | Warkentin | 198/370 |
| 5,215,179 A | 6/1993 | Warkentin | 198/365 |
| 5,223,917 A | 6/1993 | Richert | 356/407 |
| 5,237,407 A | 8/1993 | Creeze et al. | 358/107 |
| 5,286,980 A | 2/1994 | Richert | 250/560 |
| 5,401,954 A | 3/1995 | Richert | 250/226 |
| 5,474,167 A | 12/1995 | Warkentin | 198/890.1 |
| 5,988,351 A | 11/1999 | Warkentin | 198/370.04 |

FOREIGN PATENT DOCUMENTS

| | | | |
|---|---|---|---|
| DE | 3039979 A1 | 4/1982 | B07C/5/342 |
| GB | 2 021 762 A | 12/1979 | |
| GB | 2 175 396 A | 11/1986 | |

OTHER PUBLICATIONS

*Photonics Spectra*, Jul. 1997, "Hyperspectral Imaging: How Much Is Hype?", R. Winn Hardin, pp. 82–92.

* cited by examiner

Primary Examiner—Frank G. Font
Assistant Examiner—Roy M. Punnoose
(74) Attorney, Agent, or Firm—Lyon & Lyon LLP

(57) ABSTRACT

A conveying system for multiple product units conveyed on two parallel conveyors past a sensing section. The sensing section includes multiple line scan sensors which each receive input from both conveyors and a calibration standard object in a thin line scan across the conveyors. Optics include an objective lens and a 1X relay lens divided in two and including a prism between halves. The exit pupil of the objective lens is imaged onto the entrance pupil of the 1X relay lens where a slit is positioned to define an image of the thin portion of the product unit in the sensing area. The optics spread the spectrum perpendicularly to the spatial direction to define a grid received by a CCD camera. The CCD camera and associated CPU operate on the data to bin attenuated pixels, train for filtering by spectral range and employ that training to subsequently train for the establishment of algorithms which sense differences in the filter data between product units of different attributes. Various algorithms are thus prepared for determining color, maturity, blemishes, size and the like.

2 Claims, 6 Drawing Sheets

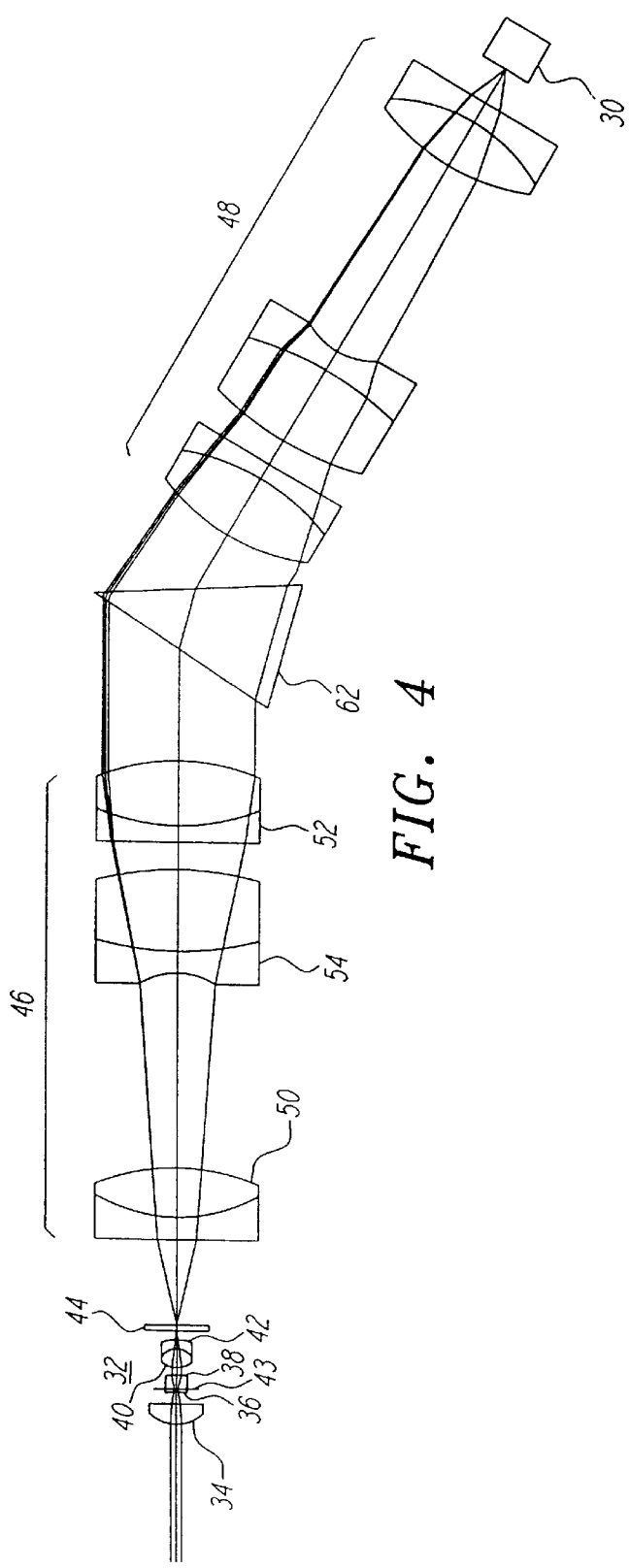
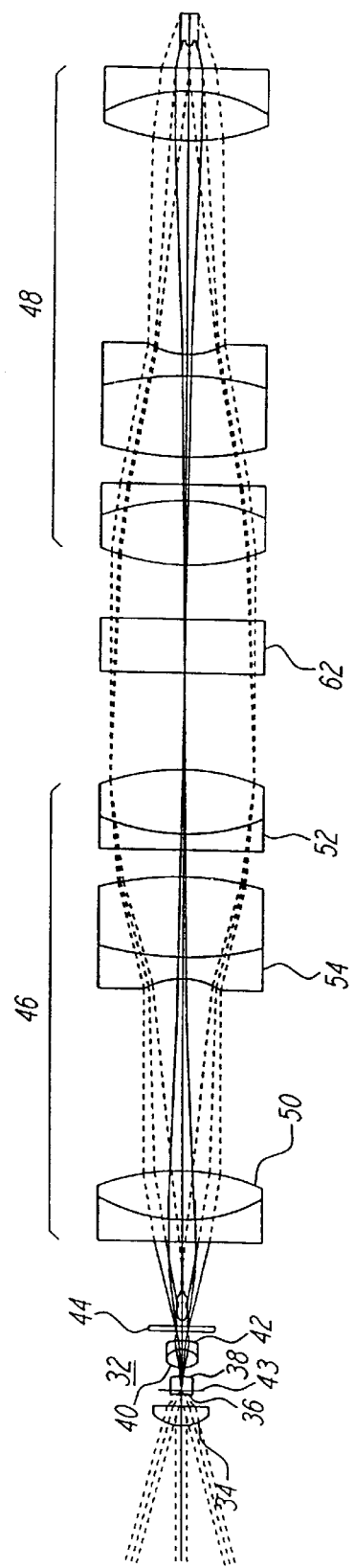

METHOD FOR DISCRIMINATION OF PRODUCE

This is a divisional application of U.S. patent application Ser. No. 09/100,286, filed Jun. 19, 1998, still pending the disclosure of which is incorporated herein by reference.

BACKGROUND OF THE INVENTION

The field of the present invention is produce discrimination based on sensed electromagnetic spectra.

Product handling activities for the discrimination of product units have long been used, particularly in the food product industry. Such discrimination has been based on size, ripeness, color, blemishes and the like. Until recent times, this activity was generally undertaken by manual labor. The versatility of workers for handling and processing large amounts and varieties of food products has generally been unsurpassed. Such processing systems typically include a conveyor passing working stations where workers distinguish and separate product units. Difficulties in finding experienced seasonal workers and the normal administrative problems associated with a fluctuating work force have long created a need for less labor intensive systems.

In defining the needs for product handling systems, as particularly applied to the food industry, the nature, volume, relative unit cost and variety of products severely impact the design of handling equipment. Most food products must be handled with great care to avoid damage. The perishable nature and large batch quantities of products in season make rapid processing a necessity. The variety of products which must be processed at different times to economically justify a food processing facility places great demand for versatility on the equipment. Thus, a substantial challenge exists in creating handling equipment to replace the versatile human worker.

An early system for handling products in a manner acceptable for automatic sorting is disclosed in U.S. Pat. No. 4,106,628 to Warkentin et al. for SORTER FOR FRUIT AND THE LIKE, the disclosure of which is incorporated herein by reference. In this patented device, cups are arranged on a chain conveyor for holding individual product units. Solenoids act to dump selected cups for product separation responsive to discriminating sensing and electronic commands. Other separating systems include devices for batting or blowing selected units from a conveyor.

In the early system of U.S. Pat. No. 4,106,628, color from a product unit is directed through lenses, fiber optics and filters to a sensing mechanism. In the actual system, light from both sides of a product unit was gathered in a single scan per product unit by two bundles of optic fibers looking from opposed sides of the product unit. Each optic fiber bundle was split and combined with a respective split portion of the other bundle. Therefore, each resulting optic fiber bundle had light from both sides of the product unit. Filters of different wavelength capacity were employed to filter the light derived from the resulting two fiber optic bundles. Red and green filters were given as examples, one filter for each resulting bundle. The signals generated by the filtered light were then compared with a standard such that a red/green color classification could be made based on the readings compared with the standard.

Another system which has been in use for some time is disclosed in U.S. Pat. No. 4,961,489 to Warkentin for PRODUCT HANDLING SYSTEM, the disclosure of which is incorporated herein by reference. In this device, a conveyor is employed which includes elements capable of tipping to off-load individual units of a product being processed. The nature of the conveyor permits some variety in shapes and sizes, including elongated products. However, a range of round or oval products in smaller sizes is not as easily accommodated by this system.

Other systems which have been in use successfully for some time are disclosed in U.S. Pat. No. 5,029,692 to Warkentin for OFF-LOADING CONVEYING SYSTEM, U.S. Pat. No. 5,195,628 to Warkentin for OFF-LOADING CONVEYING SYSTEM, U.S. Pat. No. 5,215,179 to Warkentin for OFF-LOADING CONVEYING SYSTEM, and U.S. Pat. No. 5,474,167 to Warkentin for OFF-LOADING CONVEYING SYSTEM, the disclosures of which are incorporated herein by reference. A newer device is presented in U.S. patent application Ser. No. 08/800,602, filed Feb. 19, 1997, to Warkentin for CONVEYOR, the disclosure of which is incorporated herein by reference. In these devices, a conveyor is employed which includes concave rollers defining concavities therebetween. Off-loading elements are positioned between adjacent rollers in each of the concavities. The elements are pivotally mounted about pivot axes and can be actuated to off-load product units.

A product discrimination system employing the sensing of a variety of light spectra, which may include wavelengths both in and beyond the visible spectrum, from product units being classified is disclosed in U.S. Pat. No. 5,018,864 and U.S. Pat. No. 5,106,195, both to Richert for PRODUCT DISCRIMINATION SYSTEM AND METHOD THEREFOR, and U.S. Pat. No. 5,223,917 to Richert for PRODUCT DISCRIMINATION SYSTEM, the disclosures of which are incorporated herein by reference. The system has particular utility in sorting food products such as fruits and vegetables. The magnitudes of the sensed light spectra is analyzed to determine such attributes of a product as size, ripeness, blemishes and color. A manageable amount of data is received and processed by such a system with a maximum number of product factors being determined.

In the system of U.S. Pat. Nos. 5,018,864, 5,106,195 and 5,223,917, a focused image of a product unit is directed to a fiber optic array. The array has a first end which is arranged in a rectangle. Because of this arrangement, the fiber optic cable receives what approximates a line scan image. The image may be averaged and then divided and directed through filters to provide a plurality of sensed signals for different wavelengths. Intensity may be measured for each selected wavelength spectrum. Consequently, only a few signals, the magnitude of each separately filtered portion of the image, need be processed. Methods for discriminating attributes of product units use absolute magnitudes and comparative relationships between magnitudes of various spectra of light sensed from a product unit to determine such attributes as size, color, ripeness and blemishes. Such methods may be carried out on a variety of sensing hardware including line scan cameras as well as the fiber optic system. Even a combination of such systems was suggested.

A system used with such off-loading conveyors for discriminating product units is disclosed in U.S. Pat. No. 5,156,278 to Aaron and Richert for PRODUCT DISCRIMINATION SYSTEM AND METHOD THEREFOR, the disclosure of which is incorporated herein by reference. A fiber optic system is used to sense physical attributes of the conveyed product units. A system for rotating the fruit between sensors provided added accuracy. Multiple sensing of the product is accomplished in series with a partial rotation of the product unit between each sensing and with the product stationary during each sensing. The rotation is accomplished by driving the supporting elements on the conveyor. Such rotation and multiple sensing provides substantial capabilities in the accuracy and variety of measurements derived from the process. An extended drive is provided for rotation of the supporting elements and, in turn, the product units on the conveyor prior to the sensing operation. Fruit and vegetable product units tend to be nonuniform and difficult to singulate and properly position on a conveyor. The rotation of such product units on the supporting elements tends to allow them to properly orientate, seat in a conveyor cavity and separate one from another such that sensing is enhanced.

More complicated sensing devices have been developed which use line scan cameras for determining such attributes as cross-sectional area. Such cameras have used light to present pixel information which may then be processed for summation and the like. For example, cross-sectional area may be determined by counting the number of pixels registering presence of the product unit. Such systems collect information in the form of pixel location, color or colors, and intensity, generating a substantial amount of data to be received and processed.

In a refinement of the system of U.S. Pat. No. 5,156,278 and using the features thereof, another system used with such off-loading conveyors for discriminating product units is disclosed in U.S. Pat. No. 5,286,980 to Richert for PRODUCT DISCRIMINATION SYSTEM AND METHOD THEREFOR and U.S. Pat. No. 5,401,954 to Richert for PRODUCT RIPENESS DISCRIMINATION SYSTEM AND METHOD THEREFOR WITH AREA MEASUREMENT, the disclosures of which are incorporated herein by reference. Both a fiber optic system and a line scan camera are used to sense physical attributes of the conveyed product units and the line scan camera is used for continued calibration. The two sensing systems act to measure area among attributes such as color. A comparison of the measurements for area using the two systems with the fiber optic system operating in a spectral range empirically determined to vary from the line scan camera as a function of an attribute of ripeness allows discrimination based on that attribute. The line scan camera also recalibrates on an ongoing basis by measuring a standard object and comparing the result with a standard value. Variations in products, conditions and sorting criteria can require experienced skill in changing applied spectral ranges. Also, defects are sometimes difficult to recognize because of the load of information and the sensitivity limits of the sensing systems.

SUMMARY OF THE INVENTION

The present invention is directed to a method for the discrimination of produce using electromagnetic spectra. The electromagnetic spectra is separated into spectral ranges for processing a system separating electromagnetic spectra into spectral ranges converted to a digital format is employed with algorithms to measure and compare various attributes of the product units processed. Area and other attributes recognized by different spectral ranges can be used or combined to provide discrimination based on calculated size, maturity, color, shape and damage.

In a first separate aspect of the present invention, an image of a thin portion of a product unit is passed through a slit and a prism to spread the spectrum of the image perpendicularly to the major dimension of the slit and then to a CCD camera. An array can be generated for sensing by the camera which has spatial pixels distributed in a first direction and the spectra for each spatial pixel distributed in a direction perpendicular to the first direction.

In a second separate aspect of the present invention, the foregoing aspect may further include the treatment of the entire product unit sequentially as the unit is passed by the sensing system. This product unit may more specifically be a unit of produce. Attributes of the entire unit or portions thereof may be employed for discrimination using electromagnetic spectral images.

In a third separate aspect of the present invention, a number of techniques may be uniquely employed advantageously, either independently or in combination, to manage data with a system separating electromagnetic spectra into spectral ranges for processing. Binning of data in areas of system weakness can prove useful to overcome optic and camera sensitivity. Summing of pixel counts and pixel magnitudes in selected spectral ranges can be used to reduce data storage and manipulation. The creation of histograms also provides such an effect. Ongoing recalibration through reference to a standard can accommodate nonsteady state conditions such as changes in the light source and in system temperature.

In a fourth separate aspect of the present invention, a system separating electromagnetic spectra into spectral ranges converted to a digital format is employed with algorithms to measure and compare various attributes of the product units processed. Area and other attributes recognized by different spectral ranges can be used or combined to provide discrimination based on calculated size, maturity, color, shape and damage.

In a fifth separate aspect of the present invention, filter training is used in a system separating electromagnetic spectra into spectral ranges based on selecting product units with distinguishing attributes. Scanning of such units and processing the resulting image data with a pattern recognition routine can be used to select specific spectral ranges for use in product unit processing algorithms. Data magnitude can be reduced through such a process by 98% or more without significant loss to selected sensitivity.

In a sixth separate aspect of the present invention, algorithm training based on selecting product units with distinguishing attributes is used in a system which separates electromagnetic spectra of a line scan into spectral ranges. Scanning of such units with filtering in place and processing the filtered data with a pattern recognition routine can be used for generating feature estimation algorithms. Such a routine can be applied for initial setup, changes in the product processed, changes in the conditions of the product being processed or changes in selection criteria based on amended output requirements.

In a seventh separate aspect of the present invention, optics employing a slit and a prism are arranged in conjunction with a conveyor to produce an image array for digitizing by a CCD camera. The array reflects spatial location across the conveyor in a first direction and the wavelength of the transmitted electromagnetic radiation in a second direction perpendicular to the first direction. The image intensity of the array divided into pixels by the CCD camera may be the output.

In an eighth separate aspect of the present invention, the foregoing separate aspect may further include an objective lens and a relay lens placed to either side of the slit in optical alignment and with the exit pupil of the objective lens imaged onto the entrance pupil of the relay lens to better achieve the desired spreading of the relevant spectra. The transmission and sensing of a wide range of spectra is preferred. A range of 450 nm to 1150 nm is contemplated.

In a ninth separate aspect of the present invention, any of the foregoing aspects are contemplated to be combined for advantageous application.

Accordingly, it is an object of the present invention to provide improved discrimination of product units. Other and further objects and advantages will appear hereinafter.

BRIEF DESCRIPTION OF THE DRAWINGS

FIG. 4 is a side view of an optical lens system employable with the sensing system of FIGS. 1–3.

FIG. 5 is a plan view of the optical lens system of FIG. 4.

DETAILED DESCRIPTION OF THE PREFERRED EMBODIMENT

Figure 1:
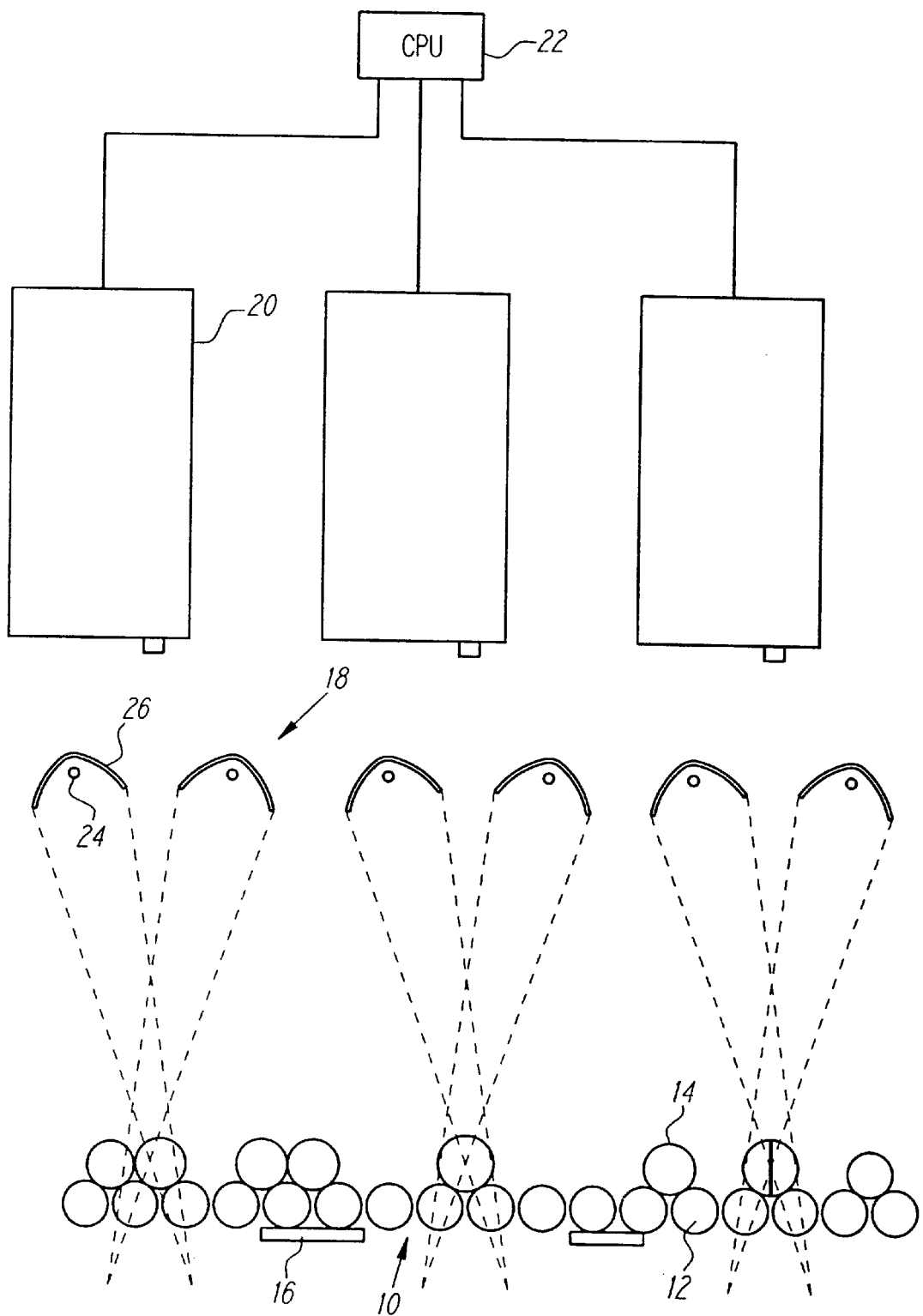
FIG. 1 is a schematic side view of a sensing system.
Figure 2:
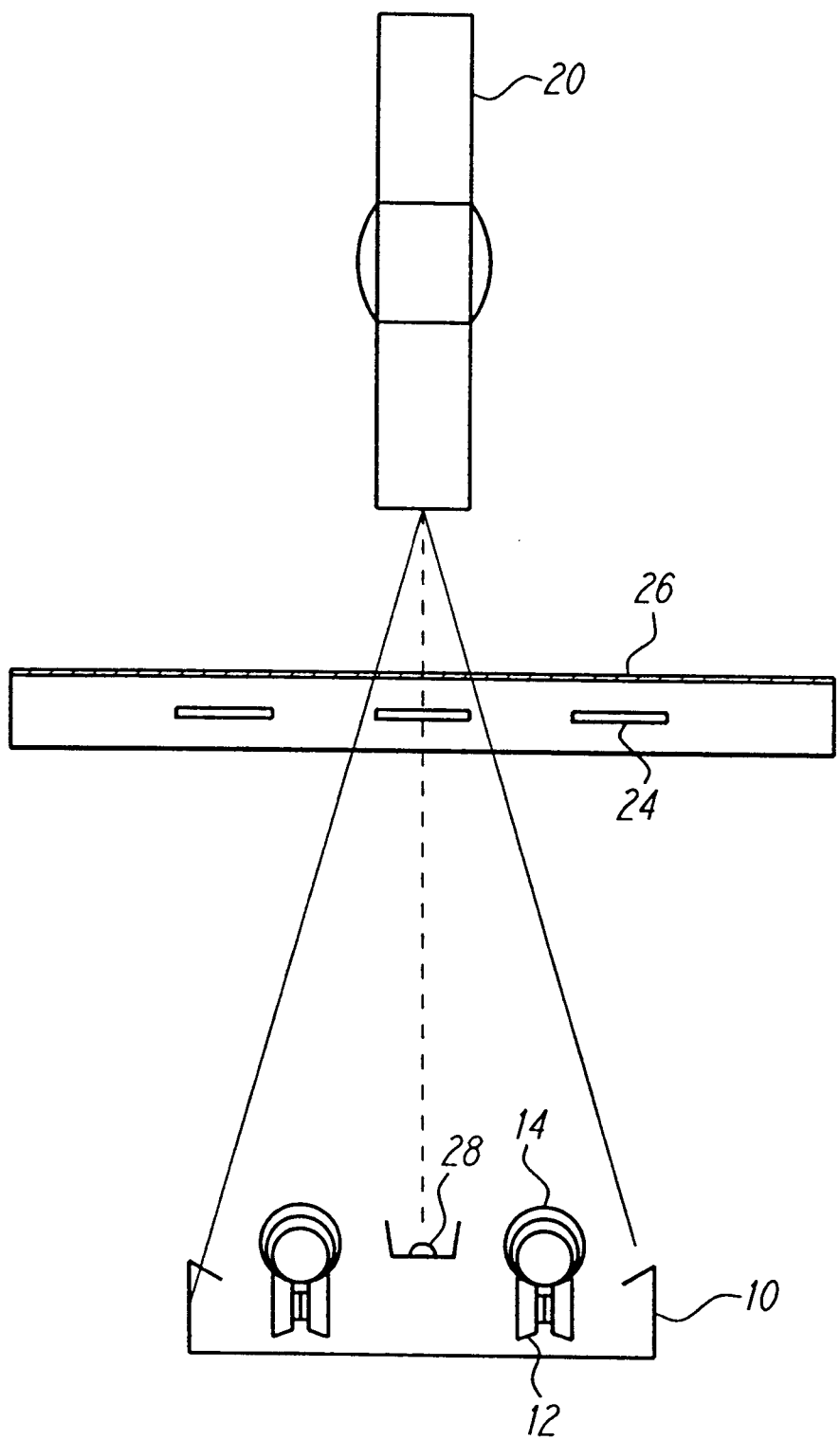
FIG. 2 is a schematic end view of the sensing system of FIG. 1.
Figure 3:
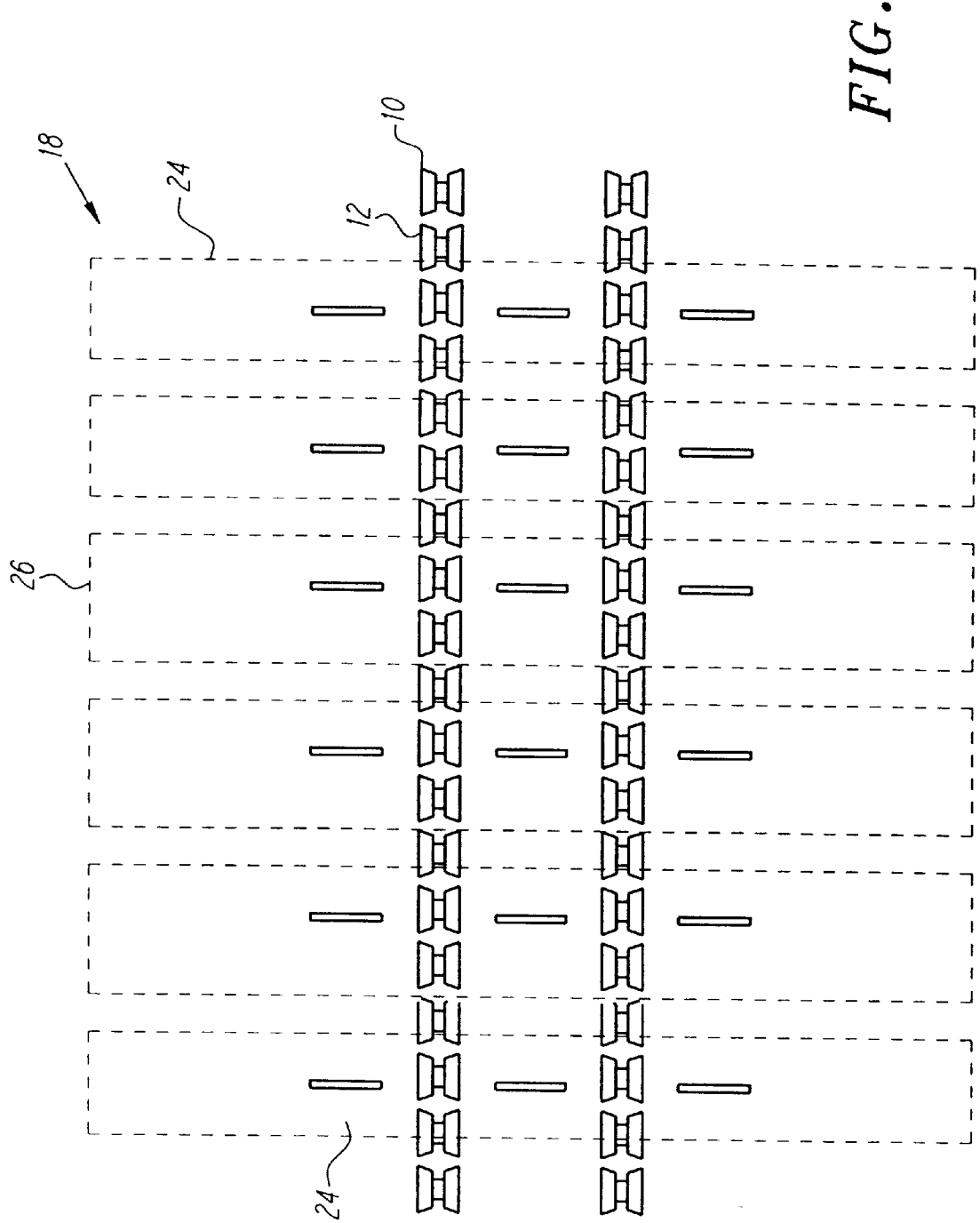
FIG. 3 is a schematic plan view of the light pattern of the sensing system of FIG. 1.

Turning in detail to the preferred embodiment, a system is disclosed which provides a sensing of product units using electromagnetic spectra. In this embodiment, the product units contemplated to be inspected are units of produce, fruits and vegetables in the broad sense. The system is most advantageously employed with off-loading conveyors such as those described in the BACKGROUND OF THE INVENTION. The conveyor stably moves product units through the sensing area. Between sensing views, the product units may be rotated to provide complete exposure to the sensing system. Off-loading mechanisms associated with the conveyor respond to control by the separator system for selectively collecting the product units along the conveying system. Actuators associated with the off-loading mechanisms divert product units from the conveyor responsive to input signals from the separator system. An indexing unit using an encoder and associated with the conveyor provides location and movement information to coordinate the sensing and off-loading functions.

Two parallel conveyors 10 run through the section. The conveyors include rollers 12 upon which product units 14 are randomly distributed. Plates 16 or other mechanisms are employed to rotate the rollers 12 between viewing positions so as to expose multiple sides of the product units. A light system, generally designated 18, provides illumination of the passing product units 14. A plurality of sensors, generally designated 20, provide line scan sensing across both conveyors 10. A CPU 22 common to all of the sensors 20 provides overall control of the conveying system and the sensed data.

The light system 18 provides a grid of illumination of the product units 14 in the sensing area. The lights employed are 225 watt incandescent light tubes 24. They are arranged in rows of four axially aligned tubes extending perpendicularly to and above the conveyor paths. The light tubes 24 are positioned within reflectors 26. The reflectors 26 are elliptical in cross section and also extend across and above the conveyor paths. The reflectors 26 are displaced from one another so that images of the product units can pass between the reflectors 26 to the sensors 20. The grid of light tubes 24 is such that there are four tubes 24 in two parallel lines around each product unit as it is being sensed.

Two or more sensors 20 are employed in the sensing section. Three is normally preferred. Rotation of the product units between the first and second sensors 20 and again between the second and third sensors 20 provide substantial coverage of the entire surface of the product unit. A fourth sensor 20 with rotation between the third and fourth sensors may be advantageous where accuracy is shown to improve significantly. The sensors 20 receive an image of the product units which is in the form of a slit one-tenth inch in the direction of travel of the product unit and extending across both conveyors 10 so as to sense adequately the full width of each product unit. As the product units 14 move along the conveyors 10, sequential thin images are exposed. The sensors 20 receive and process juxtaposed one-tenth inch thick images fully across the product units as they pass through the sensing section. The products travel at a rate requiring approximately 250 fps for the sensor.

A section of white pipe 28 is located between the conveyors 10 to act as a standard for calibration. There is one such standard object 28 for each sensor 20. As each object 28 is centrally positioned in the image area, data is received on the standard object 28 in each frame.

The sensors 20 include a CCD camera 30 with special optics best illustrated in FIGS. 4 and 5. The optics may be described as a series of optically aligned components. An objective lens 32 is developed from a split triplet design chosen for its ability to cover a large field of view with a fast relative aperture and control of chromatic aberrations over a large spectral band. The objective lens 32 in the preferred embodiment comprises five elements 34, 36, 38, 40 and 42 in three groups plus an aperture stop 43. All of the five elements contribute to image formation at the plane of a slit 44 plus aberration correction in this image. The third through fifth elements 38, 40 and 42 are forced to produce an image of the aperture stop 43 beyond the plane of the slit 44 at the location of an entrance pupil of a relay lens 46, 48. This condition eliminates the need for a field element adjacent to the plane of the slit 44. Such a field element is typically used in systems that have multiple relayed image surfaces such as the present system. Elimination of the field lens avoids the addition of strong field curvature aberrations which are difficult to eliminate and minimize distortion in the image falling on the slit plane.

The second and fifth elements 36 and 42 are made of a flint glass which has strong dispersion (change of reflective index with wavelength). These elements are used to correct for axial chromatic aberration and lateral chromatic aberration respectively. Other design forms can be made to achieve these objectives. However, they are likely to be more complex, have steeper radii, and be more expensive to fabricate. The second element 36 also provides a strong correction of the field curvature that is introduced by the remaining elements in the objective lens.

The objective lens 32 must produce an image on the plane of the slit 44 that is very sharply focused and essentially free of optical aberrations. In other words, the objective lens is self-corrected and does not rely on any aberration correction from elements in the relay lens 46, 48.

Figure 6:
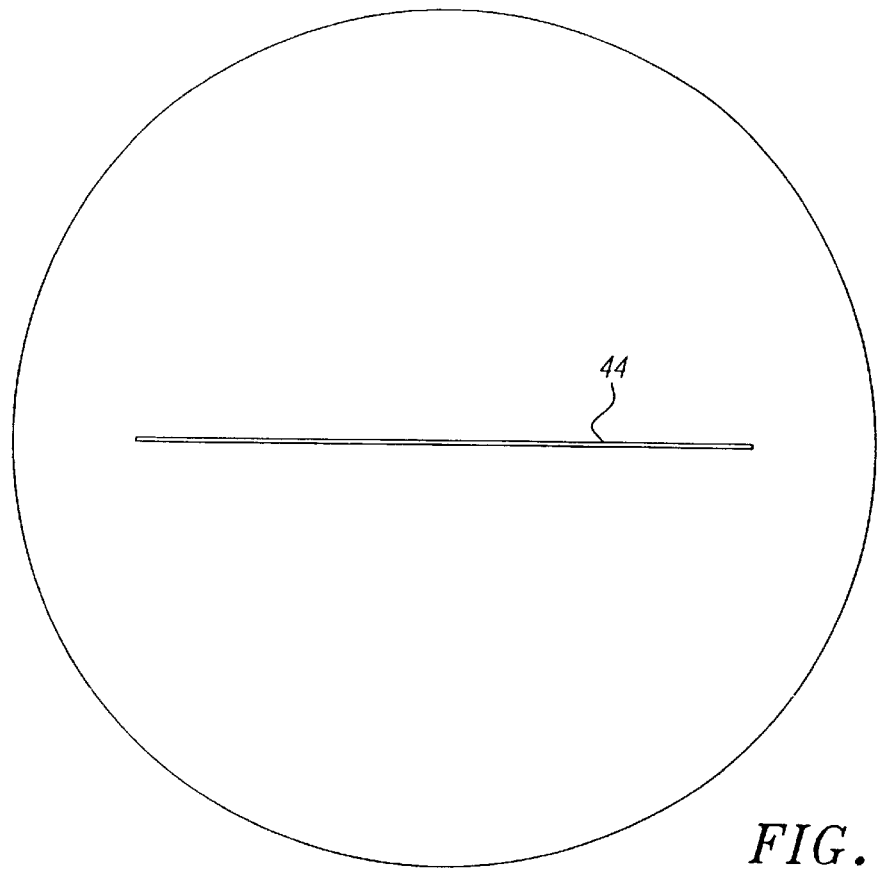
FIG. 6 is a plan view of the slit positioned in the optical lens system of FIGS. 4 and 5.

The objective lens 32 receives the image between the reflectors 26. This image is focused by the objective lens 32 at the slit 44 as seen in FIG. 6. The slit 44 is 5.0 mm×0.022 mm. In combination with the objective lens 32, the slit 44 defines the thin portion of a product unit imaged at the conveyor as 460 mm×2 mm.

The relay lens is divided into two identical halves 46 and 48 with a prism 62 located between reversed halves. By using identical lens halves to create a 1X lens, cancellation of several optical aberrations and a reduction in fabrication costs are achieved. The light from the point object is afocal between the two halves 46 and 48. The afocal condition means that the light rays from a point object are essentially parallel. This condition is also called collimation. The afocal condition advantageously accommodates the use of the dispersion prism 62 placed in the afocal space without producing strong optical aberrations. Further, the alignment of the system becomes noncritical.

Each half 46, 48 of the relay lens comprises three doublets 50, 52 and 54. Each doublet uses a crown (low dispersion) positive powered element plus a flint (high dispersion) negative powered element to correct for chromatic aberrations. The doublet 50 which is closest to the plane of the slit 44 corrects lateral chromatic aberration while the other two doublets 52 and 54 correct axial chromatic aberration. Normally two identical lens halves will correct lateral chromatic aberration by means of the system symmetry, but the presence of the dispersion prism 62 alters the system symmetry and lateral chromatic aberration correction is recovered by the doublet form. The doublet 50 near the plane of the slit 44 serves the function of helping image the objective lens exit pupil onto the relay lens entrance pupil by controlling the position of the relay lens entrance pupil. The absence of a field lens can, therefore, be attributed to the refractive power that is usually provided by the field lens being vested in the two groups in the relay and objective lenses that are nearest to the plane of the slit 44. The relay lens design uses six doublets in an arrangement providing vignetting free operation.

The resolution of the combined relay with the prism 62 is a range of 44 nm per pixel at 1150 nm in the spectrum, 8 nm at 650 nm and 4 nm at 450 nm. The first relay lens half 46 has an entrance pupil which is coincident with the exit pupil of the objective lens 32. Again, the slit 44 is positioned at the coincident location of the pupils. There is no field lens at the slit 44. The lack of a field lens eliminates strong contributions to field curvature and astigmatism aberrations that are associated with field lenses. The design of the objective lens and the relay lens are forced to image the objective exit pupil onto the relay entrance pupil by controlling the refractive power in the elements in both lens systems.

The prism 62 located between the relay lens halves 46 and 48 has an angle of inclusion of 35°. The axis of the prism is parallel to the major dimension of the slit 44. Consequently, the image of the thin portion of the product unit, effectively defining a line scan image subsequently digitized into pixels, is spread perpendicularly to the major dimension of the image to establish a spread spectrum of each spatial pixel along the image. Because of the prism 62, a substantially rectangular image is created which varies spatially along the image of the thin portion of the product unit in one direction and varies in spectral wavelength in the perpendicular direction. This spread image is presented at the image plane of the second relay lens half 48 where the CCD camera 30 is positioned. These optics are appropriately arranged in a cylindrical housing with the lens elements separated by cylindrical spacers. A non-vignetted aperture is used. The lenses are also designed to sharply focus a spectrum from 450 nm to 1050 nm.

The CCD camera 30 is a high-speed camera with one frame sampled in 0.004 seconds (250 fps). The camera has a pitch of 10 microns×10 microns with a 100% fill factor on a 512×512 array. The optics provide 490 pixels in the spectrally dispersed direction on the chip and 500 pixels in the spatial direction. This allows for modest misalignment.

With the spread spectra of the image of the thin portion of a product unit 14 recorded as an array by the CCD camera 30, the full range of electromagnetic spectra across the thin portion of product unit is digitized and identified by array location and magnitude. Wavelength is translated by this arrangement into pixel location in the spectral direction. Binning, filtering and a wide variety of algorithms can be applied to compress and select data on a real time basis which, when accumulated with the remaining thin portions of the product unit, can form the basis for discrimination by attribute for sorting.

As noted above, the spreading effected by the prism 62 is greater at the short wavelength region than at the long wavelength region. Consequently, spectral differences within the array occur because of this phenomenon. Further, the capabilities of the optics, the spectral emittance of the source and the sensitivity of the camera 30 can create other disparities in sensitivity within the array. Empirical determinations can be made through system testing to find where system weakness occurs in the sensed array. Where such areas are present, binning of pixels in the spectral direction may be introduced to increase overall sensitivity in those areas. Pixel binning enables two or more adjacent pixels in either a row or a column of the CCD camera to be summed together while being read by the camera.

The full range of spectra spread on the camera for each spatial pixel of the product unit is available for use in discriminating product attributers. However, only a portion of this spectra is needed for discrimination of any given attribute. Of course, different portions are typically necessary for different attributes. Filtering to reduce the amount of data processed to that useful portion is, therefore, possible and desirable. The selection may be of single pixels or groups of pixels, either falling within a set of desired classes. These pixels are selected in the spectral direction to be applied to each spatial position. The selections themselves are determined by an analysis of the results of sensing hand selected sample product units. The product units are selected by color or other visual indicators such as blemishes or by using measurements of various parameters established by testing the product units such as for sugar or pressure. In this way, the distinguishing product attributes can be empirically measured directly by the system from selected product units exhibiting variations in the selected attribute. It is contemplated that up to eight separate spectral points and/or ranges be used to analyze each spatial pixel.

A first mechanism by which such filtering can occur is through the foregoing empirical testing with the results being analyzed manually. Dominant spectral areas are observed and the filter selections incorporated into the CPU 22 as a memorized routine for the specific product type. Very satisfactory results can be achieved with this process.

An alternative filtering process involves the application of available pattern recognition routines through a multi-layered perceptron (MLP), a type of neural network. A selected group of product units containing one or more attributes to be recognized by the system may be used in a training exercise to allow the CPU to define the dominant spectral areas within different overall spectral ranges and synthesize outputs based on the pattern recognized. By selecting different groups of product units exhibiting different attributes, the pattern recognition routine is able to select a limited number of dominant points or ranges from the spectral patterns of all of these units for discriminating variations in the selected attributes. In this way, the number of spectral points per spatial pixel can be reduced from 490 to 8 or less of synthesized data signals reflecting the magnitudes of the selected significant patterns.

An MLP is often viewed as an interconnected network of nodes which are simple computational elements. The nodes are arranged in layers. The first layer is the input layer, the last layer is the output layer, and there are normally one or more hidden layers. The hidden layers often apply a sigmoidal function to the weighted sum of the inputs. A range of numerical values is desired for each output. This allows an operator to adjust set points. This output scheme is known as an estimation problem (as opposed to a classification problem). For estimation problems, the outputs normally perform a simple weighted sum of their inputs. The separate weights (multipliers) exist for each connection in the network. The computational structure of the MLP includes the input layer of nodes which receive input signals from each of the data points as a magnitude. The first hidden layer of nodes are each connected to every one of the input layer of nodes and are also each connected to every node in the next layer which may be another hidden layer or the output layer. Each connection represents a weighted input from the upstream node and each node in the hidden layers and in the output layer performs a summing operation. With an input of $x_i$, a hidden nodal layer with nodes $y_j$ and output nodes $z_k$, the following relationships are established:

$$y_j = \frac{1}{(1 + e^{-sum})}$$

$$sum = W_{jo} + \sum_i W_{ji} x_i$$

$y_j$ is the value associated with hidden code j.

$w_{jo}$ is the bias (offset) for hidden node j.

$W_{ji}$ is the weight (multiplier) for the connection from i-th input node to hidden node j.

$x_i$ is the i-th input $$z_k = W_{ko} + \sum_j W_{kj} y_j$$

$Z_k$ is output node K.

$W_{ko}$ is bias (offset) for output node k.

$W_{kj}$ is weight (multiplier) for the connection from the j-th hidden node to output node k.

$y_j$ is the input from the j-th hidden node.

For filter training, the inputs are the raw spectral magnitudes of the pixels for each spatial point. Associated with each such spatial point is the set of raw spectral measurements. Backpropagation is an error-minimizing training function associated with MLP which tunes the weights to generate the desired mapping. The error function used is usually the mean-squared-error over a data set. As an aid in selecting the filter regions, the result of interest is the set of weights relating the inputs to the outputs. The outputs represent the desired classes to be measured such as color, blemish and maturity. Spatial points are selected which represent various combinations of outputs. The purpose of the filtering is to identify the important portions of the input spectrum. The importance of an input $x_i$ to an output $z_k$ is determined by the sum of the weights along the various paths from the input to the output. This can be written as $$z_k = \sum_j (W_{ji} W_{kj}) x_i$$

A plot of $z_{ki}$ magnitude vs. i would identify the regions of the spectrum important to the output $z_k$. k such plots can be used to identify filter regions important to simultaneously measuring the k outputs.. This can be done either interactively through an operator or automatically by correlating the plots and identifying the peaks.

In a separate training operation, the filtered results can be subjected to a further pattern recognition step. This second step provides a mechanism for establishing algorithms to separate the product units by attribute. With the filtering already accomplished, the routine for establishing the selection of filtered points for applying to appropriate algorithms is greatly simplified. Hand selected sample product units are used to exemplify the attributes of interest. These selected product units are sensed. The resulting filtered profiles are analyzed to establish patterns indicative of product attribute which can then be incorporated into the sorting algorithms by hand.

Alternatively, the analysis and selection of patterns can be processed by a pattern recognition routine. Of course, the data resulting from the initial filter learning operation may be used for this operation or new data taken. Again, the application of available pattern recognition routines through a multi-layered perceptron (MLP) may be used. The routine determines the differences between separate groups of filtered data which are presented such that the program itself identifies the spectral patterns to be used in the sorting algorithms.

For algorithm training, the inputs are the filter outputs. The outputs are the same outputs used for filter training and the training process is very similar. In this case, however, the optimized algorithm that results is the signal which is used to determine the discrimination of the product unit. The algorithm generates output measurements (such as color, blemish, and maturity) for each spatial point. These measurements are in turn used by the system to make the appropriate selections of the product units. Note that the MLP algorithm is given as one example. There are many other possibilities along with the heuristic approach where the algorithm is defined by a training operator and based on intuition.

A number of attributes may be discerned from analysis of electromagnetic spectra of the product units. Accumulations of such spectra in various forms by the CPU 22 are employed for product discrimination and sorting. Color is possibly the most obvious produce sorting attribute discernable from analysis of electromagnetic spectra. Color may be categorized by a summation of the number of spatial pixels falling within a spectral range exceeding a threshold value. The absence of a second color may also be of interest to such an analysis. More refined color can be accomplished through a binning of magnitudes for a selected spectral range above a threshold value or within a bounded range of magnitudes. Multiple ranges may be used in an additive sense where appropriate.

The size or weight of the product unit may be quite accurately determined by a summation of pixels defining what amounts to the cross-sectional area of the unit scanned. Where appropriate, the length may also be incorporated in determining volume. Shape may also be determined through, for example, a summation of thin widths to suggest a long neck.

Blemishes may also be detected through a threshold pixel count in a spectral range predetermined to indicate bruising, rot or other adverse localized feature.

Less obvious attributes such as a deteriorating core on certain apples may also be recognized through a combination of spectral indicators. Certain spectral lines appear to change with maturity, causing more or less light absorption in certain spectral ranges. A comparison of the magnitudes of the pixels in such ranges with the pixel count in a spectral range indicative of presence of the product unit independent of product attributes will indicate variations in the magnitude relative to the cross-sectional area as a function of ripeness.

The accumulation of data in certain forms can provide the input for the foregoing calculations. A summation may be maintained of the number of pixels detected above a minimum threshold intensity. Spectral ranges may be selected which do not vary with other attributes associated with the product unit, useful for area calculations. Alternatively, spectral ranges may be used which specifically indicate sizes of specific attributes. The lengths of each thin-scan area image of a product may be accumulated as the product moves through the scanning section. The number of such scans taken between product beginning and product end may also be accumulated to establish product length.

The magnitudes of electromagnetic intensity above a threshold may also be summed for selected points or ranges. In addition, histograms can be generated which sum the intensities of pixels within different spectral ranges which fall above a threshold or within an intensity range.

By maintaining running totals or calculated running total values, the amount of data to be manipulated in real time is reduced over maintaining information about each pixel for later summation on each product unit. With binning and filtering, the array generated by the optical system provides for no more than the magnitude of eight synthesized data points for each of 500 pixels as measured in the spatial dimension. With eight filtered points per spatial pixel in a single line scan of the thin image, manipulation and entry into one or more of the various summations and commands is most manageable on a real time basis. As the juxtaposed thin scan image is then received, the same number of values are again manipulated and an appropriate output generated.

To insure that the CCD camera remains in calibration in spite of fluctuations in temperature, light conditions and the like, the standard object 28 is repeatedly measured for width within the thin scan area based on a pixel count. The value observed for the cross-sectional width of the white target object 28 is compared with a standard maintained within the CPU 22. If the count varies from that standard, the duration of the image is expanded or contracted to again arrive at the standard value for the observed reading. Drifting is avoided by this technique.

Figure 7:
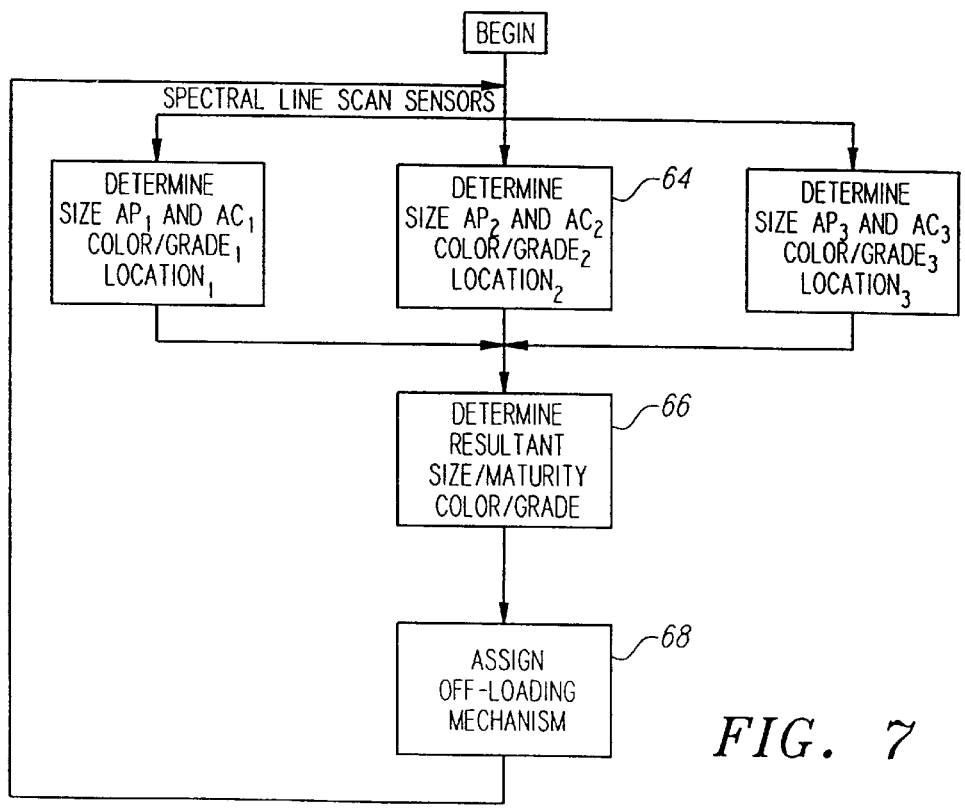
FIG. 7 is a logic flow chart of the separator system.

Applying the foregoing in practice, FIG. 7 provides a logic flow chart for the overall sensing system. The routine begins at the step 64. Three spectral line scan sensors serially view a product unit as it passes through each thin-scan area of the sensing section. The sensors are coupled with the CPU 22 where information is gathered and sorted based on indexing with the conveyor. In the step 66 the resultant accumulation from all three or more spectral line scan sensors is determined such as by averaging or averaging with the discarding of extreme values. Once appropriately categorized, an off-loading mechanism is assigned at the step 68 and the product unit continues along the conveyor until off-loaded at that mechanism. The routine is then recycled. However, it must be recognized that the system is capable of handling multiple units at one time. In this way, the units do not need to be spaced apart to the extent that only one passes through all line scan sensors before the next such unit is introduced.

Figure 8:
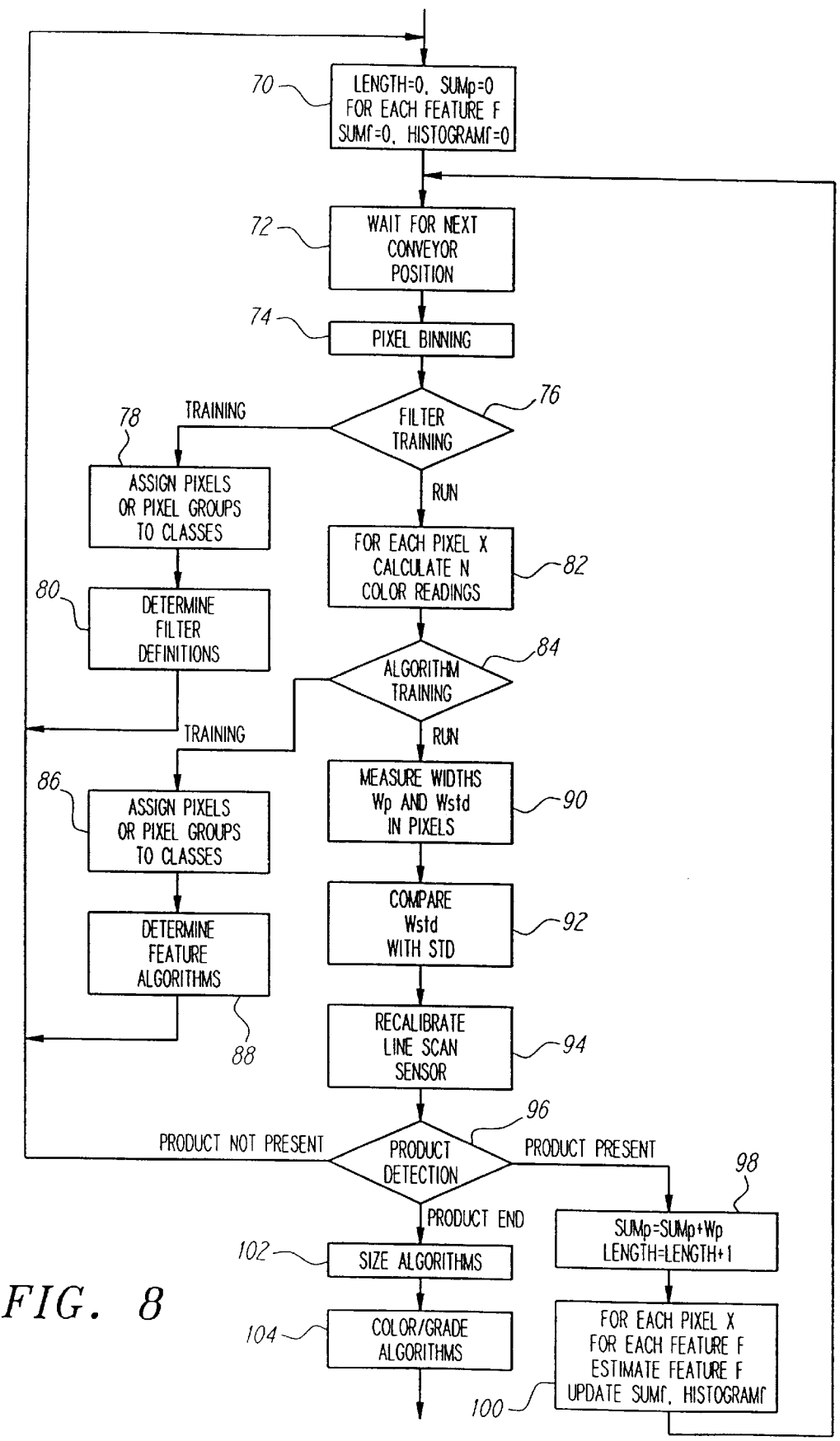
FIG. 8 is a detail logic flow chart of each sensor.

FIG. 8 is a further detail of the step 64 as applied to any one of the spectral line scan sensors effectively defined by the optics, the cameras 30 and the CPU 22. In the step 70 the system is initialized with all values equal to zero in anticipation of a new product unit 14 passing through the sensing section. In the step 72, the next index position is sensed to initiate the remainder of the process.

The CCD camera employed allows pixel binning as discussed above. In the present application, pixel binning is performed in the spectral dimension in the step 74. The illumination from the tungsten lamps and the responsivity of the CCD camera are not uniform across the spectrum. Regions of the spectrum with low illumination levels and low responsivity will be binned in order to even out the response across the spectrum.

The step 76 processes the sensed data in one of two ways depending on the mode setting of the device. The device may be set on filter training such that raw data is employed in the training process. If the system is in the normal run mode, data will simply proceed onto a first level of manipulation.

Instead of training the system in a single manipulation, two separate manipulations are used. The first is undertaken in the steps 78 and 80. A pattern recognition routine is employed for filter training. Selected product units are run through the system screening section where products are sensed to define various points or ranges of pixels in the spectral direction. The sampling may be done either by visually selecting images of multiple products such as color or surface defects or by using measurements of various parameters such as sugar or pressure, also from multiple product units. The standard pattern recognition algorithms of the step 80 are than employed to resolve the data accumulation in the step 78 to achieve a selection of various spectral points and/or regions to act as filters of the raw data, converting 490 pixel readings per spatial pixel into up to 8 separate categories or points. Numerous sets of samples are recorded at step 78 before the calculations of step 80 are performed.

Once filter training is accomplished, the mode of the system is adjusted such that the step 76 leads to the step 82 where the large quantity of spectral information is compressed to a much smaller number. This is accomplished by applying the categories of points and ranges as established in the steps 78 and 80. This filtering is able to reduce the amount of data accumulated by a factor of two magnitudes.

The filtered data then progresses to the step 84 where another mode selection of training or running is encountered. When training, the filtered data is presented in the step 86 where the pixels and groups of pixels are assigned to a set of desired classes. This is done by again running product units through the sensing section to load in the profiles of selected attributes. In the step 88, standard pattern recognition algorithms are used to determine algorithms for estimating the desired features from the compressed image data. Numerous sets of samples are recorded at step 86 before the calculations of step 88 are performed.

When not in the algorithm training mode, the step 84 determines product presence and the estimation of selected features. When running, the step 84 leads to the step 90 where a selected spectral range is employed which does not vary with color, ripeness or the like. The number of pixels in the spatial direction measuring the presence of a product unit are summed to establish the width of the thin portion of the product unit being imaged as $W_p$. At the same time, the width $W_{std}$ of the standard object 28 is also measured in pixels.

In the step 92, the measured width $W_{std}$ of the standard object 28 is compared with a standard STD. In the step 94, the line scan camera is recalibrated to expand or contract the period of each sensing step as a means for achieving recalibration such that $W_{std}$ is again comparable with the width standard STD.

At the step 96, algorithms are present to detect the beginning and the end of each product unit. Appropriate routing either returns the system to the step 70 where no product is present, begins or continues the summing process before recycling to the step 72 when the product is present or provides some concluding algorithms before continuing on to the step 66. Further, at the step 96, an algorithm for detecting and discriminating between two products that touch is used to identify the units as two separate objects.

When a product is present, the number of pixels indicating the product is present at that pixel are summed as $W_p$ and added to the prior $SUM_p$, if any. The length which is an incremental unit for each successive juxtaposed thin portion of product unit defined by each frame is accumulated through the addition of one unit per cycle. In the step 100, multiple features may be calculated for each pixel. These features represent measurements of various product characteristics such as color, surface blemishes and sugar. Maturity may be established in conjunction with the step 98 as previously discussed. A $SUM_f$ for each of the features is maintained. Histograms are updated for each feature.

Once the product end is established, the size is determined based on an estimated volume calculated in the step 102 from the cross-sectional area defined in the step 98. In the step 104, minimum criteria for the various summed and calculated amounts established in the step 100 are compared with the accumulated amount for the product unit being measured. Each piece of product is checked against the grade criteria with the best grade being considered first. The product unit is selected for the grade for which it first qualifies. Hierarchy in grading can also be established so that classes and subclasses may be graded. For example, ripe fruit may be distinguished from immature fruit and the ripe fruit then divided into large, medium and small sizes.

Accordingly, a system for the discrimination of product units particularly applicable for produce is presented. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A method for measuring maturity of a unit of produce, comprising moving the unit of produce past a sensing station along a conveying path;

separating the image of the unit of produce received at the sensing station into electromagnetic spectral images;

measuring the cross-sectional area of the image of the unit of produce in a spectral range indicative of the presence of the image of the unit of produce at the sensor independently of the color of the unit of produce;

accumulating the total magnitude of at least one selected electromagnetic spectral range of the image of the unit of produce which deviates from a fixed ratio with the measure cross-sectional area as a function of maturity of the unit of produce;

comparing the total magnitude of the at least one selected electromagnetic spectral range of the unit of produce and the calculated cross-sectional area of the unit of produce with a feature estimation algorithm;

successively passing images of juxtaposed thin portions of the product unit through a slit, separating different electromagnetic spectral images including successively passing the images of the thin portions of the product unit from the slit through a prism to spread the spectrum of the images perpendicularly to the major dimensions of the images;

successively digitizing the magnitudes of the spread images by a CCD camera in pixels, the measuring of the cross-sectional area including summing the pixels of the images of the unit of produce, the accumulating the total magnitude including measuring the magnitude of the filtered electromagnetic spectral range of each pixel of the images of the unit of produce and summing the measured magnitudes.

2. The method of claim 1 further comprising passing a calibration image of a thin portion of a standard object through a slit;

comparing the calibration image with a calibration standard;

recalibrating the CCD camera based on the comparison.

* * * * *